United States Patent [19]

Pridgen

[11] 4,454,774

[45] Jun. 19, 1984

[54] METHOD OF SAMPLING A LIQUID IN A CONTAINER

[75] Inventor: Robert L. Pridgen, Palestine, Tex.

[73] Assignee: Aluminum Company of America, Alcoa Center, Pa.

[21] Appl. No.: 336,728

[22] Filed: Jan. 4, 1982

[51] Int. Cl.³ .......................... C25B 1/00; G01N 1/14
[52] U.S. Cl. .............................. 73/863.81; 73/864.51; 204/67; 204/128
[58] Field of Search ................. 73/863.81, 863.85; 204/400, 245, 67

[56] References Cited

U.S. PATENT DOCUMENTS

| 2,344,859 | 3/1944 | Fox | 204/61 |
| 3,412,613 | 11/1968 | Brown et al. | 73/863.85 |
| 3,642,603 | 2/1972 | Sakai et al. | 204/220 X |
| 3,747,411 | 7/1973 | McDermott et al. | 73/863.85 X |
| 3,890,214 | 6/1975 | Kleveland | 204/245 X |
| 4,133,727 | 1/1979 | Rodgers, Jr. | 204/64 R X |
| 4,140,594 | 2/1979 | Rodgers, Jr. | 204/67 |
| 4,338,177 | 7/1982 | Withers et al. | 204/245 X |

FOREIGN PATENT DOCUMENTS 2012722  5/1982  United Kingdom ................ 204/245

*Primary Examiner*—Daniel M. Yasich
*Attorney, Agent, or Firm*—Jones, Tullar & Cooper

[57] ABSTRACT

In a method of sampling a liquid in a container, a sample of the liquid is collected through a sample gathering assembly part of which extends into the liquid. The sample gathering assembly includes a gas-containing, liquid-remote portion, which is situated further from the liquid than a gas-containing, liquid-near portion thereof. Before collecting the sample, steps are taken to create a greater pressure in the gas-containing, liquid-remote portion of the sample gathering assembly than exists in the gas-containing, liquid-near portion thereof. Then, the liquid-remote portion is opened to the liquid-near portion and the collecting is performed.

10 Claims, 1 Drawing Figure

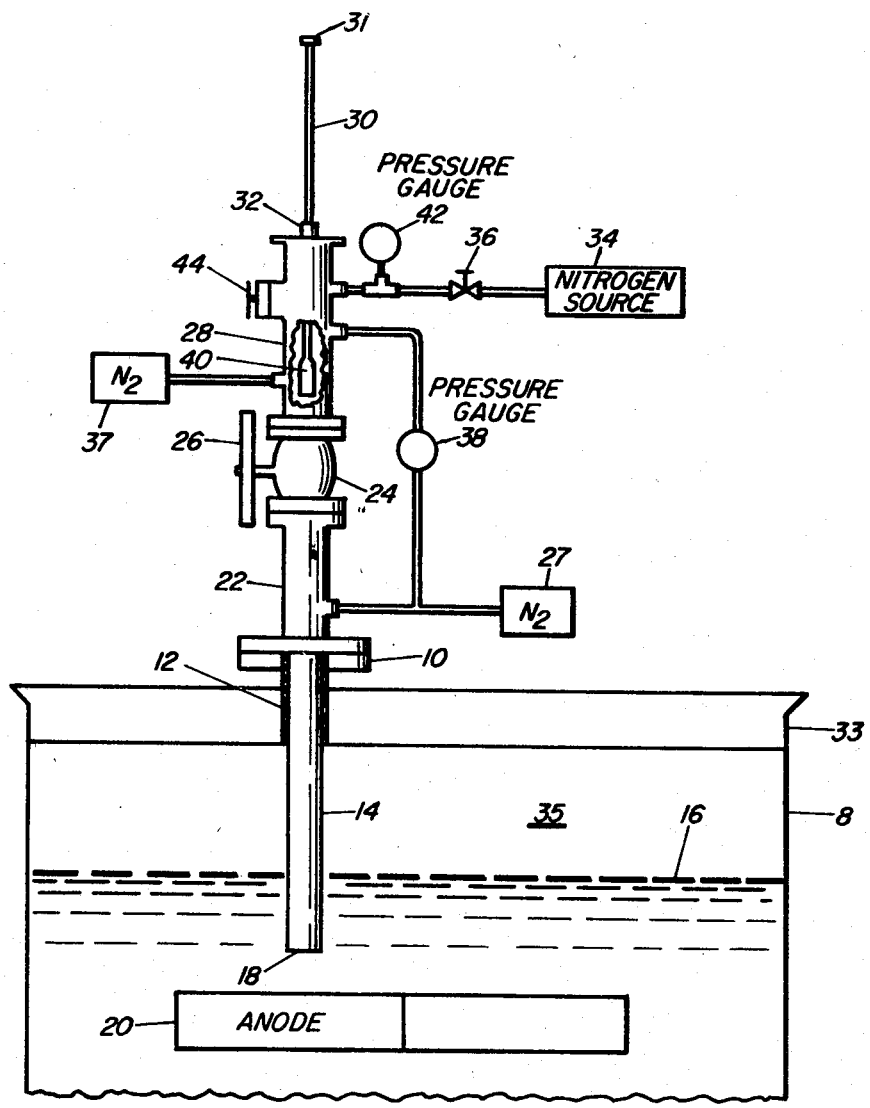

METHOD OF SAMPLING A LIQUID IN A CONTAINER

BACKGROUND OF THE INVENTION

The present invention relates to a method of sampling a liquid in a container and more particularly to sampling of a molten salt in a closed container under variable pressure.

U.S. Pat. No. 4,140,594 of Rogers et al. issued Feb. 20, 1979 for "Molten Salt Bath Circulation Patterns in Electrolysis" shows in its FIG. 1 a container for molten salt and is an instance where the present invention can be put to use. Cell containers for chloride electrolysis as disclosed in the 4,140,594 patent are closed to prevent chlorine escape and to keep moisture out. The molten salt bath can have a composition, for example, as follows, in weight percent: NaCl 51.0, LiCl 40.0 AlCl$_3$ 6.5, MgCl$_2$ 2.5, and will be typically at around 715° C., so that aluminum resulting from AlCl$_3$ electrolysis occurs in molten form. It has been the practice to collect molten salt samples through a tube extending through a port in the lid of such cell down into molten salt above the cell anode. A difficulty encountered is that the pressure in the headspace above the bath can be unexpectedly high, so that, when the valve is opened for running a sample thimble down into the bath to fill the thimble with a sample, the bath can surge up the tube and freeze in the colder parts of the system. When this happens, the sampling system must be partially dismantled and either washed out or else heated to get rid of the solid salt plugs.

SUMMARY OF THE INVENTION

An object of the invention is to provide a new and improved method of sampling a liquid in a container, and more particularly for sampling molten salt in an electrolysis cell which is closed and which can contain molten salts under varying degrees of pressure.

These as well as other objects which will become apparent in the discussion that follows are achieved according to the present invention by providing, in a method of sampling a liquid in a container, including the step of collecting a sample of the liquid through a means extending into the liquid, the improvement including the steps of creating a greater pressure in a gas-containing, liquid-remote portion of the tube than exists in a gas-containing, liquid-near portion thereof and then opening the liquid-remote portion to the liquid-near portion and carrying out the collecting.

BRIEF DESCRIPTION OF THE DRAWING

The sole FIGURE is a partially schematic, elevational view of a portion of an electrolysis cell illustrating an embodiment of the invention.

DESCRIPTION OF THE PREFERRED EMBODIMENTS

Referring to the FIGURE, the invention is illustrated in the context of a cell container 8 for producing aluminum and chlorine by the electrolysis of AlCl$_3$. Such a cell container is more fully disclosed in the above-mentioned 4,140,594. The cell has a port 10 in which is held, by a suitable packing gland 12, a silicon oxynitride (e.g. S-80 material of Norton Company, Worcester, Mass.) tube 14 extending as a seal leg down into a molten salt bath 16. The lower end 18 of the tube is separated, e.g. a distance of 3 inches, from the uppermost plate 20 in the cell, which is in this embodiment an anode. This anode restricts access to deeper regions of bath 16.

In sealed connection to, and above, port 10, there is arranged a metal tube 22. Sitting on its upper end is a valve 24 of the type involving a ball which can be turned by handle 26 to selectively align a cylindrical bore in the ball with tube 22 and sample port box 28. A flow of nitrogen gas is fed into tube 22 (which is always open to tube 14) from source 27 so that, if there is any leakage through valve 24 when it is in its closed position, excess pressure in headspace 35 cannot cause molten salt bath to move up into the colder portions of tube 14 where it might freeze and plug the system, due to the fact that the temperature in tube 14 above the bath 16 is not at the molten temperature of the bath 16. Instead, the flow from source 27 bubbles out lower end 18 and keeps bath out of tube 14, as long as valve 24 remains closed.

The portion of the apparatus shown below the valve 24, represents a liquid-near portion of the apparatus, while the portion above the valve 24 represents a liquid-remote portion of the apparatus.

Extending into the sample port box 28 through fitting 32 is a sample rod 30.

In the method of the present invention, when it is desired to take a sample of molten salt, valve 36 is opened to a source of auxiliary gas, e.g., compressed nitrogen source 34, until the delta-pressure gage 38 indicates that the pressure in the gas in the sample port box 28, remote from the molten salt bath 16, is, e.g. 15 inches water column greater than the pressure in the gas in tube 22, near bath 16. Provision of this excess pressure prevents the possibility that the pressure in headspace 35 could force molten bath to the level of the water-cooled cell lid 33 or even higher, where the bath could freeze, to plug the system with solid bath when valve 24 is opened for sampling. The water cooling of the lid may be such that the temperature of the underside of the lid is maintained at 120° F. (about 50° C.). See U.S. Pat. Nos. 3,642,603 and 4,133,727.

With the excess pressure imposed, valve 24 is opened and rod 30 is lowered until stop 31 contacts fitting 32. The length of rod 30 is chosen such that holder 40 brings a sample thimble (not shown) to within e.g. 10 inches of lower end 18 in the lowered position of the rod when stop 31 is in contact with fitting 32. Fitting 32 (e.g. a PO Gland, catalog number PG5-500 Type B, of the Corax Corporation of Buffalo, N.Y. bears on rod 30 with an adjustable tightness, so that gas can escape to allow the rod to slide even when valve 24 is closed, in order to permit holder 40 to be kept low in the sample port box 28 for storage or brought high for removal of a sample thimble through port 44. The purposeful looseness at fitting 32 also permits a flow of nitrogen from source 37 to keep the interior of box 28 dry; this flow from source 37 is kept on at all times, both when valve 24 is open and when it is closed.

The nitrogen flow rates from sources 27 and 37 are small relative to the gas leakage possible through fitting 32. In contrast, the nitrogen flow rate possible from source 34 is large relative to such leakage. When valve 24 is opened, the pressure difference measured by gage 38 goes to 0 and the reading on pressure gage 42 will drop also. Nitrogen source 34 has sufficient ability to supply gas, however, that nitrogen actually flows to push bath out of lower tube end 18, upon the opening of valve 24, and to keep it out until valve 36 is partially closed down, as will be explained shortly. In contrast, the flows from sources 27 and 37 would both escape through fitting 32 and have essentially no effect on the level of bath within tube 14, if valve 24 were opened without source 34 turned on via valve 36.

With rod 30 still in its lowered position, valve 36 is next turned in the valve closing direction to decrease the $N_2$ pressure, until the pressure reading on gage 42 drops e.g. on psi. This will allow the bath to rise, e.g., approximately 18.4 inches into tube 14 collecting the liquid so as to immerse holder 40 with molten bath, this resulting in the filling of the sample thimble in the holder 40. This leaves, e.g., still 22 inches of tube length, before the bath would reach the level of lid 33.

The approximately 18.4-inch rise of the bath in tube 14 results from the following considerations. With valve 24 open, $$P_1 = P_2 + BL \times 1.5,$$

where $P_1$-the pressure read on gage 42 expressed in inches water column, $P_2$-the pressure in headspace 35 expressed in inches water column, BL-bath level outside tube 14 minus the bath level inside tube 14, 1.5-the specific gravity of the bath.

When the $N_2$ purge thrugh valve 36 is decreased until $P_1$ drops one psi (27.7 inches water column), the bath rises inside tube 14 a distance of 18.4 inches (27.7/1.5 equals 18.4). With this controlled rise of bath within tube 14, a sample is caught without necessity of extending the rod below end 18 of the tube 14.

Valve 36 is then opened to bring the $N_2$ pressure back to where it was before the one psi drop. Then the rod is brought back to a raised position and valve 24 is closed. Following this, valve 36 is closed and the sample port box 28 opened at port 44 to permit removal of the sample thimble from holder 40.

The temperature in the tube 14 above the bath 16 and in the tube 22 is below the freezing point of the bath.

While the invention has been described in terms of preferred embodiments, the claims appended hereto are intended to encompass all embodiments which fall within the spirit of the invention.

What is claimed is:

1. In a method of sampling a liquid in a container, including the step of collecting a sample of the liquid through means extending into the liquid, said means defining a liquid-near portion and a liquid-remote portion when viewed relative to the liquid in the container, said liquid-near portion being open to the liquid and being connected to said liquid-remote portion, the improvement comprising the steps of:

applying a gas to the liquid-near portion of said means;

applying a gas to the liquid-remote portion of said means;

creating a greater pressure in a gas-containing, liquid-remote portion of said means than exists in the container and in the gas-containing liquid-near portion thereof;

opening the liquid-remote portion of said means to the liquid-near portion thereof; and reducing the pressure in both portions of said means in order to carry out the step of collecting sample of the liquid.

2. A method as claimed in claim 1, wherein said means includes a tube of said liquid-near portion which extends into the liquid, and wherein the step of collecting a sample of the liquid includes receiving liquid in said tube as a result of the step of reducing the pressure in both the portions of said means.

3. A method as claimed in claim 1, further including the step of providing the container with a closed headspace.

4. A method as claimed in claim 1, further including the step of permitting the temperature in said means to fall below the freezing point of the liquid in the direction from the liquid-near portion to the liquid-remote portion of said means.

5. A method as claimed in claim 1, further including the step of providing structure within the container for restricting access of said means to deeper regions of the liquid.

6. A method as claimed in claim 1, wherein an auxiliary gas is provided to create the greater pressure in the gas-containing, liquid-remote portion of said means, the quantity of the auxiliary gas being such that the liquid is effectively kept out of said means following the step of opening the liquid-remote portion of said means to the liquid-near portion thereof, and wherein the pressure in both portions of said means is reduced by lowering the pressure of the auxiliary gas in said portions.

7. A method as claimed in claim 1, further including the step of providing an electrolysis plate within the container for restricting access of said means to deeper regions of the liquid.

8. A method as claimed in claim 7, said liquid being molten salt.

9. A method as claimed in claim 8, aluminum being electrolytically produced in the container.

10. A method as claimed in claim 8, chlorine being electrolytically produced in the container.

* * * * *

UNITED STATES PATENT AND TRADEMARK OFFICE
CERTIFICATE OF CORRECTION

PATENT NO. : 4,454,774

DATED : June 19, 1984

INVENTOR(S) : Robert L. Pridgen

It is certified that error appears in the above—identified patent and that said Letters Patent are hereby corrected as shown below:

Col. 3, line 9          Change "on" to --one--.

Signed and Sealed this

Eleventh Day of December 1984

[SEAL]

Attest:

GERALD J. MOSSINGHOFF

Attesting Officer      Commissioner of Patents and Trademarks